United States Patent [19]

Vanlerberghe et al.

[11] 4,014,990

[45] * Mar. 29, 1977

[54] ANIMATED-γ-DIALDEHYDES IN HAIR STRENGTHENING COMPOSITIONS

[75] Inventors: Guy Vanlerberghe, Montjay-La-Tour par Claye-Souilly; Georges Rosenbaum, Asnieres, both of France

[73] Assignee: Societe Anonyme dite: L'Oreal, Paris, France

[ * ] Notice: The portion of the term of this patent subsequent to May 21, 1991, has been disclaimed.

[22] Filed: Apr. 24, 1974

[21] Appl. No.: 463,808

Related U.S. Application Data

[62] Division of Ser. No. 210,217, Dec. 20, 1971, Pat. No. 3,812,246.

[30] Foreign Application Priority Data

Dec. 24, 1970 Luxembourg .......................... 62317

[52] U.S. Cl. .......................... 424/70; 260/247.7 Z; 260/293.89; 260/347.3; 260/563 C; 260/567.6 M; 260/576; 260/577; 260/584 R; 424/DIG. 1; 424/DIG. 2; 424/47; 424/59; 424/63; 260/247.7 T; 260/247.1 E

[51] Int. Cl.$^2$ .......................... A61K 7/66
[58] Field of Search .................. 132/7; 8/10.2, 11; 424/70

[56] References Cited

UNITED STATES PATENTS

| | | | |
|---|---|---|---|
| 3,158,542 | 11/1964 | Kalopissis | 8/10.2 X |
| 3,781,418 | 12/1973 | Pomot et al. | 424/63 |

*Primary Examiner*—Albert T. Meyers
*Assistant Examiner*—Vera C. Clarke
*Attorney, Agent, or Firm*—Cushman, Darby & Cushman

[57] ABSTRACT

Aminated γ-dialdehyde and the quaternary ammonium salts thereof are prepared by acid hydrolysis of their respective corresponding 2.5-dialkoxy 3-amino 4-hydroxy tetrahydrofurans or by acid hydrolysis of their respective corresponding tetraalkyl acetals. The aminated γ-dialdehydes and the quaternary ammonium salts thereof are usefully employed in cosmetic compositions to tan the skin or to strengthen or restructure the hair.

11 Claims, No Drawings

ANIMATED-γ-DIALDEHYDES IN HAIR STRENGTHENING COMPOSITIONS

This is a division, of application Ser. No. 210,217 filed Dec. 2, 1971, now U.S. Pat. No. 3,812,246.

The present invention relates to a γ-dialdehyde having the formula

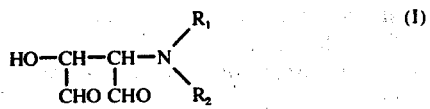

wherein $R_1$ and $R_2$ each independently are selected from the group consisting of hydrogen, alkyl, hydroxyalkyl, cycloalkyl, aryl, alkaryl, (2,5-dialkoxy-4-hydroxy)-3-tetrahydrofuryl wherein each of the alkoxy moieties has 1 - 4 carbon atoms, β-N-[(2,5-dialkoxy-4-hydroxy)-3-tetrahydrofuryl]-aminoethyl wherein each of the alkoxy moieties has 1 - 4 carbon atoms, and together with the nitrogen atom to which they are attached form a heterocycle selected from the group consisting of piperdinyl and morpholinyl. Representative alkyl substituents are those having 1 - 6 carbon atoms while useful hydroxalkyl substituents are those wherein the alkyl moiety has 1 - 6 carbon atoms such as hydroxyethyl. Representative cycloalkyl substituents include those having 3 - 6 carbon atoms and especially cyclohexyl, whereas useful aryl substituents include phenyl, naphthyl and the like. The alkyl moiety of the alkaryl substituent can have, preferably, from 1 - 6 carbon atoms while the aryl moiety can be, for instance, phenyl, naphthyl or the like. A preferred alkaryl substituent is benzyl.

The present invention also relates to the quaternary ammonium salts of the γ-dialdehydes of formula (I), said quaternary ammonium salts having the formula

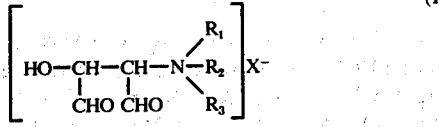

wherein $R_1$ and $R_2$ each independently are selected from the group consisting of alkyl, hydroxyalkyl, cycloalkyl, aryl, alkaryl, (2,5-dialkoxy 4-hydroxy)-3-tetrahydrofuryl wherein each of the alkoxy moieties has 1 - 4 carbon atoms, β-N-[(2,5-dialkoxy 4-hydroxy)-3-tetrahydrofuryl]-aminoethyl wherein each of the alkoxy moieties has 1 - 4 carbon atoms, and together with the nitrogen atom to which they are attached form a heterocycle selected from the group consisting of piperidinyl and morpholinyl. Representative alkyl substituents are those having 1 - 6 carbon atoms and, advantageously, methyl or ethyl. Useful hydroxyalkyl substituents are those wherein the alkyl moiety has 1 - 6 carbon atoms, such as hydroxyethyl. Representative cycloalkyl substituents include those having 3 - 6 carbon atoms and, especially, cyclohexyl. The aryl moiety of the alkaryl substituent can have, preferably, from 1 - 6 carbon atoms while the aryl moiety again can be phenyl, naphthyl or the like. A preferred alkaryl substituent is benzyl. $R_3$ represents a member selected from the group consisting of lower alkyl having 1 - 4 carbon atoms and benzyl, substituted or not and $X^-$ represents a member selected from the group consisting of chloride, bromide, iodide, methosulfate, ethosulfate, paratoluene, sulfonate and methane sulfonate. A preferred value for $R_3$ is methyl while preferred values for $X^-$ are chloride, methosulfate, paratoluene, sulfonate and methane sulfonate.

The above γ-dialdehydes of formulae (I) and (II) correspond to 2-amino-3-hydroxy aldehyde and to the N-substituted derivatives thereof.

The present invention also relates to the preparation of the γ-dialdehydes having formula (I) and of the quaternary ammonium salts thereof having formula (II).

Further, the present invention also relates to a cosmetic composition containing at least one aminated γ-dialdehyde having formula (I) and/or at least one quaternary ammonium salt thereof having formula (II).

The aminated γ-dialdehydes of formula (I) can be prepared by acid hydrolysis of a 2,5-dialkoxy 3-amino 4-hydroxytetrahydrofuran and the N-substituted derivatives thereof having formula

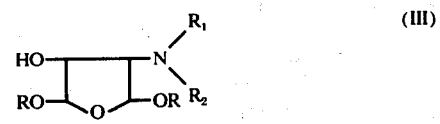

wherein $R_1$ and $R_2$ have the same meanings as in formula (I) and R represents alkyl having 1 to 4 carbon atoms, preferably, methyl.

The quaternary ammonium salts of aminated γ-dialdehyde having formula (II) can be prepared by acid hydrolysis of the quaternary ammonium salts of N-disubstituted 2,5-dialkoxy 3-amino 4-hydroxy tetrahydrofurans having the following formula

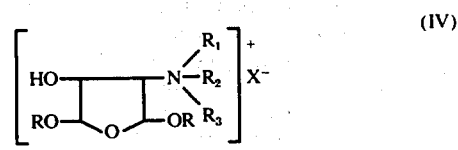

wherein $R_1$, $R_2$, $R_3$ and $X^-$ have the meaning indicated above for the compounds of formula (II) and R represents an alkyl having 1 - 4 carbon atoms, preferably methyl.

In the acid hydrolysis reaction medium the concentration of the compound having formula (III) or (IV) to be hydrolyzed can vary within wide limits and, preferably, a concentration of 0.01 to 1 mole/liter is employed.

There is heated, for example, in a boiling water bath, an acid solution of the compound having formula (III) or (IV) for a time that can range from about 5 minutes to several hours. The acid medium is obtained by addition of a strong mineral or organic acid, such as HCl, $H_2SO_4$, paratoluene sulfonic acid or methane sulfonic acid up to a concentration of about 0.1 to 5 N. The reaction mass is generally heated to a temperature of about 20° to 100° C.

The aminated γ-dialdehydes of formulae (I) and (II) can also be prepared by acid hydrolysis of their corresponding tetraalkyl acetals having formulae (V) and (VI), respectively.

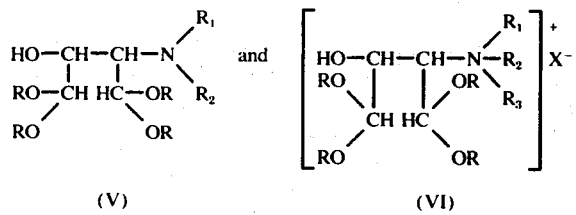

(V) and (VI)

In formula (V), $R_1$ and $R_2$ have the meanings indicated for the compound of formula (I) and R represents an alkyl having 1 – 4 carbon atoms, preferably methyl. In formula (VI) $R_1$, $R_2$, $R_3$ and $X^-$ have the meanings indicated for the compounds of formula (II) and R represents an alkyl having 1 – 4 carbon atoms, preferably methyl.

Once the hydrolysis reaction has been terminated, these solutions respectively, contain aminated γ-dialdehydes of formula (I) or quaternary ammonium salts of formula (II) depending on whether the starting compound was of formula (III) or (V), or a compound of the formula (IV) or (VI).

The solutions which result from the hydrolysis reaction yield characteristic reactions of aldehydes, such as reduction of hypoidite, formation of oximes and dinitrophenylhydrazones.

The aldehydes in the hydrolyzed solutions are characterized either by their reaction with dinitrophenylhydrazine to produce a dinitrophenylhydrazone or by hypoiodite determination.

In the first case there is employed an excess of solution of 0.2% 2,4-dinitrophenylhydrazine in 2N HCl, and after a period of standing the dinitrophenylhydrazones that are formed are separated by filtration. They are then washed with 2N HCl, dried and analysed.

In the second case the procedure followed is that embodied in the method adopted by Robinson and McLeod, which is described in Loiseleur's book, "Laboratory Technique," page 1344 (Masson Edition).

The aminated γ-dialdehydes of formula (I) are only stable in strongly acid solution, with the primary amino compounds being less stable than the secondary and tertiary compounds.

It is to be noted that the 2,5-dialkoxy tetrahydrofurans and their derivatives represented by formulae III and IV present cis-trans isomerism at the level of the alkoxy groups in positions 2 and 5. The substituents in positions 3 and 4 can likewise increase the number of possible isomers. The isomers often are detectable by gas chromatography and sometimes they can be isolated by fractional distillation.

Certain of the 2,5-dialkoxy tetrahydrofurans of formula (III) are new compounds. They are those wherein R represents alkyl having 1 to 4 carbon atoms, preferably the methyl radical; and wherein $R_1$ represents hydroxyalkyl, cycloalkyl, aryl, alkaryl radical having up to 12 carbon atoms, (2,5-dialkoxy 4-hydroxy)-3tetrahydrofuryl and β-N-[(2,5-dialkoxy 4-hydroxy)-3-tetrahydrofuryl]-aminoethyl and wherein $R_2$ represents hydrogen or the immediately above meaning indicated for $R_1$. In these new tetrahydrofurans, the alkyl moiety is hydroxyalkyl and the alkaryl radical preferably is cyclohexyl, while the preferred aryl substituent is phenyl, the preferred hydroxyalkyl substituent is hydroxyethyl and the preferred alkaryl substituent is benzyl.

2,5-dialkoxy 3-amino 4-hydroxy tetrahydrofurans especially N-substituted derivatives thereof having formula (III), quaternary ammonium salts having formula (IV), tetraalkyl acetal having formula (V) and quaternary ammonium salts of tetraalkyl acetals having formula (VI) are valuable intermediate products which by way of acid hydrolysis allow to obtain useful solutions for the preparation of cosmetic compositions, particularly for the coloring of the skin and the strengthening or the reconstructing of the hair.

The salts of the 2,5-dialkoxy 3-ammino 4-hydroxy tetrahydrofurans of formula (IV) are also new compounds.

Moreover, the aminated γ-dialdehydes of formula (I) and their quaternary ammonium salts having formula (II) are also new compounds.

The 2,5-dialkoxy tetrahydrofurans and their N-substituted derivatives of formula (III) can be prepared according to the following methods A and B.

METHOD A

Reaction of an amine having the formula

wherein $R_1$ and $R_2$ have the meanings indicated for the compound of formula (III) on a 2,5-dialkoxy-3,4-epoxytetrahydrofuran having formula (VIII) wherein R represents alkyl having 1 to 4 carbon atoms.

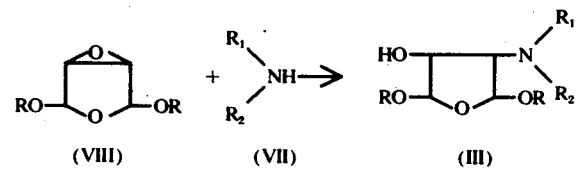

(VIII)    (VII)    (III)

The 2,5-dialkoxy-3,4-epoxy tetrahydrofuran of formula (VIII) can, in turn, be prepared from 2,5-dialkoxy-3-halogeno-4-hydroxytetrahydrofuran having formula (IX) below, in which Hal designates chlorine or bromine and R has the meaning indicated above.

In practice, to effect reaction A, a procedure in accordance with (a) or (b) is followed:

a. USE OF THE AMINE IN STOICHIOMETRIC QUANTITY

There is heated at a temperature between 50° and 100° C, for example, in a boiling water bath for several hours, preferably between 20 and 110 hours, a mixture which contains a 2,5-dialkoxy-3,4-epoxy tetrahydrofuran and a stoichiometric quantity of the amine, either without solvent or in aqueous or aqueous alcoholic solution. At the end of the heating period the solvent is evaporated off if required, and the compound of formula (III) is isolated by distillation, crystallization or any other appropriate method. The aqueous alcohol solution can comprise between about 10 to 90 percent of an alcohol such as methanol, ethanol or isopropanol.

b. USE OF EXCESS AMINE

In this alternative procedure, after the end of the heating period the remaining amount of amine is driven off under reduced pressure, as well as the solvent if necessary, and the product is isolated as indicated above. Generally, the molar ratio of amine to epoxy tetrahydrofuran will range from about 50:1 to 1.5:1.

METHOD B

Reaction of an excess of the amine having formula VII wherein $R_1$ and $R_2$ have the meaning indicated above, preferably, in the presence of an alkali metal hydroxide, such as sodium or potassium hydroxide with a compound having formula (IX), according to the following scheme:

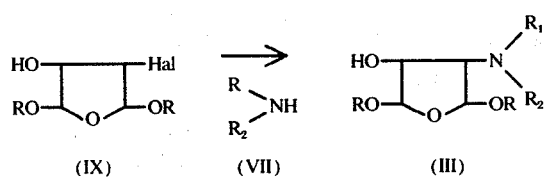

The alkali metal hydroxide can be used in stoichiometric or in slight excess with respect to compound (IX).

To effect reaction B, a procedure in accordance with (c) or (d) is followed.

c. INTRODUCTION OF ALKALINE METAL HYDROXIDE AFTER HEATING

There is heated in a boiling water bath, for example, for several hours, preferably between 20 and 110 hours, a reaction mixture which contains a 2,5-dialkoxy-3-halogeno-4-hydroxytetrahydrofuran [compound of formula (IX)] and an excess of the amine having formula (VIII). The molar ratio amine : tetrahydrofuran ranges from 50:1 to 2:1 and preferably, there are used 5 moles or more amine per mole of compound of formula (IX). An aqueous or an aqueous alcoholic solution as defined above can be employed. The concentration of the amine solution is not of primary importance, but it is preferable to use a solution wherein the amine concentration ranges between about 5 to 10 moles/liter.

After the end of the heating period there is added in the form of a 10 N solution, an alkali metal hydroxide, such as sodium or potassium hydroxide, in equimolar quantity with reference to the compound of formula (IX) which was originally introduced. This is followed by evaporation to dryness under reduced pressure. The residue is taken up in alcohol such as ethyl alcohol and the mineral salts are eliminated by filtration. There is a repeated evaporation to dryness under reduced pressure. The compound of formula (II) is separated from the residue by distillation, crystallization or by any other suitable separation technique.

d. INTRODUCTION OF THE ALKALINE METAL HYDROXIDE BEFORE HEATING

As a variant of procedure (c), sodium hydroxide or potassium hydroxide is introduced at the start, before heating is commenced. The remaining procedure is that described above for procedure (c).

The present invention also relates to a process for the preparation of the quaternary ammonium salts of formula (IV) by reaction of a quaternizing agent $R_3X$ on a compound havng formula (III). As quaternizing agent there can be used Lower $C_1$-$C_4$ alkyl halides, substituted or unsubstituted benzyl halides, lower dialkyl sulfates, lower alkly tosylates and lower alkyl mesylates, said lower alkyls having 1 to 4 carbon atoms. This reaction is effected according to the following scheme:

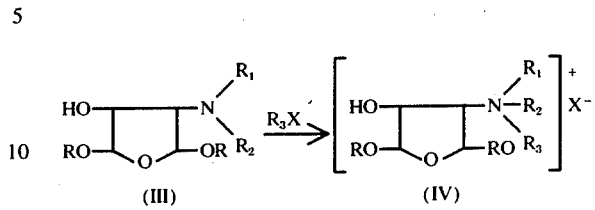

There is added, for example, drop by drop, to a compound of formula (III) in ether solution, with cooling, a stoichiometric quantity of the quaternizing agent. The quaternary ammonium salt separates out. The mixture is allowed to stand, the solvent is decanted, the residue is washed with ether, and thereafter is dried under vacuum.

The present invention further relates to the use of (1) aminated γ-dialdehydes of formula (I), (2) the quanternary ammonium salts of formula (II), (3) the acid hydrolysis product of a 2,5-dialkoxy-3-amino-4-hydroxy tetrahydrofuran or its N-substituted derivative of formula (III), (4) the acid hydrolysis product of a quaternary ammonium salt having formula (IV), (5) the acid hydrolysis product of a tetraalkyl acetal having formula (V), and (6) the acid hydrolysis product of the quaternary ammonium salt of a tetraalkyl acetal having formula (VI), for the coloring of the skin and the strengthening or the restructuring of the hair.

It has been found that aminated γ-dialdehydes, of the present invention impart to the skin a color which is similar to that which it acquires by more or less lengthy exposure to the sun or to ultraviolet rays. The ability of the aldehydes of the present invention to color the skin varies according to the degree of substitution of the amino group and according to the nature of the substituents.

It has also been observed that the most active compounds are the secondary amines and next the primary amines and then the tertiary amines. Quaternary compounds do not color the skin but are usefully employed to strengthen or restructure the hair.

The present invention thus also relates to a cosmetic composition for coloring the skin comprising a cosmetic carrier and at least one aminated γ-dialdehyde whose N atom is nonsubstituted, mono-substituted or disubstituted. The pH of this composition can range from 2 to 7, preferably between 2 and 5. The cosmetic carrier can be, for instance, an aqueous solution, an aqueous alcoholic solution containing, for instance, about 10% – 90% of a lower alkanol such as ethanol and isopropanol, an oleo alcohol creme, a gel or a fluid emulsion called "milk." Moreover, it can be packaged under pressure in an aerosol container together with an aerosol propellant such as dichlorodifluoromethane, trichloromonofluoromethane, mixtures thereof or other conventional aerosol propellants. Additionally, the cosmetic composition can also include such conventional adjuvants as perfumes, thickening agents or dispersing agents. The active γ-dialdehyde component, as set forth in (1) – (6) immediately above, is generally present in amounts of about 0.5% to 12% percent by weight of the skin coloring or tanning composition.

The aminated γ-dialdehydes of the present invention effect a strengthening, restructuring or regeneration of the hair, with an improvement of its cosmetic quality.

This regeneration or restructuring generally is effected on bleached hair or on hair that has undergone a treatment for permanents. It also can be used on hair which has undergone a reduction that constitutes the first stage of a "permanent wave" operation and before the second stage thereof, that is to say, the neutralizing operation.

This restructuring or strengthening of the hair is evidenced by a better appearance and an improved feel, softness and liveliness of the hair and general improvement of its cosmetic quality.

Usually this treatment to strengthen or restructure the hair is effected by applying to the hair a cosemtic composition containing at least one aminated γ-dialdehyde of formula (1) and/or a quaternary ammonium salt of formula (2), the pH of the solution being between 1.5 and 9, preferably between 2 and 5 and permitting said composition to remain in contact with the hair for a period of about 5 – 60 minutes at a temperature generally between about 15° and 50° C. The hair is then rinsed and if desired rolled on curlers and dried.

Thus the present invention also relates to a cosmetic composition for strengthening or restructuring the hair, said composition comprising an aqueous or aqueous alcoholic solution of about 20 to 70 weight percent of an alkanol such as ethanol or isopropanol of at least one aminated γ-dialdehyde of formula (1) and/or a quaternary ammonium salt of formula (2), the pH of the solution being between 1.5 and 9, preferably between 2 and 5. The γ-dialdehyde or its quaternary ammonium salt is generally present in amounts of about 2 to 25 and preferably 3 to 18 percent by weight of said composition.

Such a composition can include other cosmetic ingredients and be in the form of a solution, a creme or a gel. It also can be stored under pressure in aerosol containers together with an aerosol propellant such as dichlorodifluoromethane, trichloromonofluoromethane, their mixtures as well as other conventional aerosol propellants.

In order to better illustrate the invention, the following examples of the preparation of the compounds of this invention and their use are given below.

EXAMPLES OF PREPARATION

Preparation of compounds of formula (III)

EXAMPLE 1

Method A - procedure (a), preparation of 3,3'-ethylene diamino-bis-(2,5-dimethoxy-4-hydroxytetrahydrofuran) having formula:

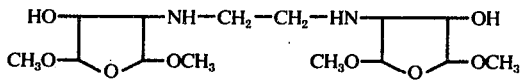

There is heated in a boiling water bath for 108 hours a mixture of:
29.2 g of 2,5-dimethoxy 3,4-epoxy tetrahydrofuran
6.08 g of 98.5% ethylene diamine and
3.5 ml of water The development of the reaction is followed by gas chromatography. After the conclusion of the heating period the water is driven off under pressure, and reagents that have not reacted are eliminated by distillation under 0.1 mm Hg, heating by means of an oil bath at 200° C. As distillation residue there is obtained 31.65 g of the compound indicated above, in the form of a syrupy red liquid.

EXAMPLE 2

Method A - procedure (b), preparation of 2,5-dimethoxy 3-piperidino 4-hydroxytetrahydrofuran having the formula:

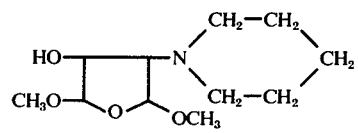

There is heated in a boiling water bath for 48 hours, a mixture of:
14.6 g of 2,5-dimethoxy 3,4-epoxy tetrahydrofuran
55 ml of piperidine
7 ml of water After the conclusion of the heating period the water and excess piperidine are driven off under reduced pressure and the product is distilled. 19.3 g of the compound indicated above are obtained.

EXAMPLE 3

Method B - procedure (c), preparation of 2,5-dimethoxy 3-amino 4-hydroxy tetrahydrofuran having the formula:

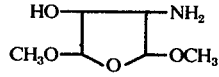

There is heated in a boiling water bath for 20 hours a mixture of 27.4 g of 2,5-dimethoxy 3-chloro 4-hydroxytetrahydrofuran and 300 ml of concentrated NH$_4$OH (22° Be). During this heating period there are added in five operations at regular time intervals 150 ml of NH$_4$OH. After conclusion of the heating period there are added 15 ml 10 N NaOH, with evaporation to dryness under reduced pressure. The residue is taken up in ethyl alcohol, filtered and distilled under vacuum. There are obtained 19.25 g of the compound indicated above.

EXAMPLE 4

METHOD B - procedure (d), preparation of 2,5-dimethoxy 3-ethylamino 4-hydroxytetrahydrofuran having the formula:

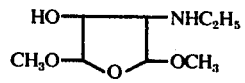

There is heated in a boiling water bath for 24 hours a mixture of:
18.25 g of 2,5-dimethoxy 3-chloro 4;1 -hydroxytetrahydrofuran
91 ml of 5.48 N ethylamine
10 ml of 10 N NaOH After 5 hours of heating there are added 45.5 ml of ethylamine as supplement.

After the conclusion of the heating period the solution is evaporated to dryness under reduced pressure. The residue is taken up in alcohol and the mineral salts are eliminated by filtration. Evaportion to dryness under reduced pressure is repeated and by distillation, 15.3 g of the compound indicated above are isolated.

Table 1 below summarizes Examples 1 – 18 illustrating the preparation and properties of the compounds of formula (III) (including the 4 compounds described above).

The different columns of the said Table 1 indicate the Example No., the values of $R_1$, $R_2$, $R_3$, Method of preparation (A or B) and procedure (a,b,c, or d), duration of the heating in hours, yield in %, boiling point, in ° C/mm Hg., melting point, in ° C; percentages of C, H and N by elementary analysis, percentage of n by protometry and calculated values for percentages of C, H and N.

Insofar as the melting and boiling points are concerned, it is to be noted that, as indicated above, the compounds of formulae (III) and (IV) present cis-trans isomerism at the level of the methoxy groups in positions 2 and 5. The substituents in positions 3 and 4 can also increase the number of possible isomers. In the course of preparation of these compounds, no attempt was made to separate the isomers and for this reason the boiling points are often spread over a range of temperatures that is somewhat broad. Further the melting points are not particularly significant because they were determined on mixtures of isomers whose proportion may vary from one procedure to the next.

It is to be noted that the melting points above 50° C were determined on a Koffler bench: melting points below 50° C were not determined.

The compound of Example 14 was imperfectly separated from the starting amine, the mixture containing 78% of the compound of Example 14 and 22% of the starting amine. These percentages were determined by measurement of the nitrogen. Preparation of compounds of formula (IV)

EXAMPLE 19 preparation of [(2,5-dimethoxy 4-hydroxy) tetrahydrofuryl 3-trimethyl ammonium] methosulfate having the formula:

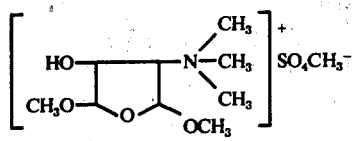

To 1.6 g of 2,5-dimethoxy 3-dimethylamino 4-hydroxytetrahydrofuran in 10 ml ether, there is added drop by drop with cooling, 0.88 ml of dimethyl sulfate. The quaternary ammonium salt separates very rapidly. The mixture is allowed to stand for 2 hours and then the solvent is decanted. The residue is washed twice with ether and dried under reduced pressure. 2.53 g of the above indicated quaternary ammonium salt are collected, representing a 96% yield.

EXAMPLE 20

Using an alternative procedure to a solution of 20.3 g of 2,5-dimethoxy 3-dimethylamino 4-hydroxytetrahydrofuran in 30 ml acetone, there is added, drop by drop, a solution of 12.6 g dimethyl sulfate in 30 ml acetone. The resulting solution is left standing at ambient temperature for 16 hours. Then the mixture is heated to boiling for 3 hours. An abundant precipitate is formed. The reaction mixture is then cooled to −20° C and filtered thereby providing a yield of 85%, i.e. 26.8 g of the above quaternary ammonium salt exhibiting a melting point of 122° C.

The result of analysis of this compound appears in Table 2.

EXAMPLE 21 preparation of [(2,5-dimethoxy 4-hydroxytetrahydrofuryl 3-dimethyl benzyl ammonium] chloride having the formula:

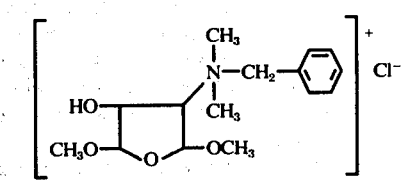

A solution of 20.2 g of (2,5-dimethoxy 3-dimethylamino 4-hydroxy) tetrahydrofuran in 40 ml acetone is mixed with a solution of 12.7 g benzyl chloride in 20 ml acetone. The resulting solution is left standing for 2 hours at ambient temperature, after which it is heated under reflux for 4 hours. The reaction mixture is then allowed to cool to room temperature and the precipitate that forms is filtered therefrom.

20.3 g of the quaternary ammonium salt of the above formula which represents a 64% yield is obtained, the salt exhibiting a melting point of 178° C.

The result of the analysis of this compound appears in Table 2.

EXAMPLE 22 preparation of [(2,5-dimethoxy 4-hydroxy) tetrahydrofuryl 3-methyl diethyl ammonium] paratoluene sulfonate, of the formula:

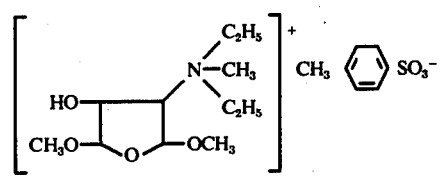

A solution of 13.0 g 2,5-dimethoxy 4-hydroxy 3-diethylaminotetrahydrofuran in 25 ml methylethylketone is mixed with a solution of 10.6 g of methyl paratoluene sulfonate in 25 ml methylethylketone. The solutions are left in contact for 16 hours. The precipitate that forms is filtered, and there is obtained 8.5 g of the sought compound. Melting point: 142° C.

The mother liquors are heated to boiling for 5 hours, then cooled to −20° C. The precipitate that forms is filtered and recrystallized in acetone. There is thus obtained 7.2 g of the compound, melting point = 138° C.

Total yield is 68%.

Results of the analysis appear in Table 2.

EXAMPLE 23 preparation of [(2,5-dimethoxy 4-hydroxy) tetrahydrofuryl 3; -methyl morpholinium] paratoluene sulfonate having the formula:

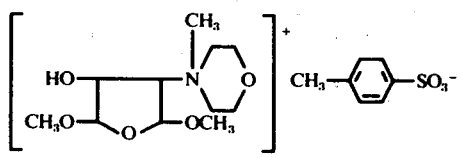

A solution of 23.9 g 2,5-dimethoxy 4-hydroxy 3-morpholino tetrahydrofuran in 50 ml methylethylketone is mixed with solution of 18.6 g dimethyl paratoluene sulfonate in 30 ml methylethylketone. The resulting solution is heated at reflux for 9 hours. The solvent is then evaporated under reduced pressure and the residue is taken up in 350 ml water. This aqueous solution is then clarified with activated charcoal, commercially available as "Norit," and the water is evaporated under reduced pressure. The residue is crystallized in a 1 : 2 mixture of acetone and ethyl acetate. There are obtained 24.9 g of the above product exhibiting a melting point of 124°/128° C, which amount represents a 60% yield.

The result of the analyses appears in Table 2.

EXAMPLE 24 preparation of [(2,5-dimethoxy 4-hydroxy tetrahydrofuryl 3-methyl piperidinium]methane sulfonate having the formula:

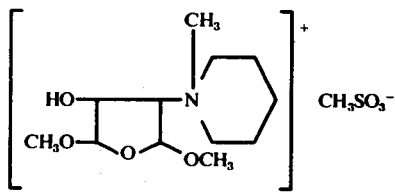

A solution of 23.3 g of (2,5-dimethoxy 4-hydroxy 3-piperidino) tetrahydrofuran in 50 ml methylethylketone is mixed with a solution of 11 g of methyl methane sulfonate in 30 ml methylethylketone. The resulting mixture is heated to reflux for 7 hours after which it is cooled to $-20°$ C. 27.8 g of the above compound are obtained in crystalline form, melting at 120°–122° C, and representing a yield of 82%.

The results of the analysis appears in Table 2.

Table 2 below summarizes the characteristics of the quaternary ammonium salts of formula (IV) prepared above.

The different columns of Table 2 indicate the Example No., the values of $R_1$, $R_2$, $R_3$ and X, the melting point, in °C, the percentage found for the various constituents: C, H, N and Cl, by elementary analysis as well as the theoretical percentages (calculated values).

PREPARATION OF AMINATED DIALDEHYDES HAVING FORMULAE (I) AND (II)

Aldehydes of formulae (I) and (II) are prepared by acid hydrolysis of corresponding compounds of formulae (III) and (IV). Some examples of hydrolysis are presented in the use examples which appear hereinafter.

Some of these aldehydes have been characterized by preparing their bis dinitrophenyl hydrazone hydrochloride.

Table 3 summarizes the characteristics of these compounds.

In this Table appear the meaning of $R_1$ and $R_2$, melting points with decomposition, percentage contents of C, H, N by elementary analysis as well as their theoretical percentages (calculated values) and finally the corresponding formula.

TABLE 1

| Ex. No. | $R_1$ | $R_2$ | $R_3$ | Method of Preparation | Heating Period (Hours) | Yield % | Boiling Point ° C/mm Hg. | Melting Point ° C |
|---|---|---|---|---|---|---|---|---|
| 3 | H | H | — | B(c) | 20 | 79 | 90–98/0.1 | 66 |
| 5 | H | —CH₃ | — | B(c) | 20 | 62 | 87–91/0.3 | 58 |
| 4 | H | —C₂H₅ | — | B(d) | 24 | 80 | 98–100/0.5 | <50 |
| 6 | H | —C₃H₇ | — | B(d) | 28 | 84 | 85–95/0.08 | 52 |
| 7 | H | —CH(CH₃)₂ | — | B(d) | 44 | 58 | 99–102/0.9 | 62 |
| 8 | H | —C₄H₉ | — | B(d) | 44 | 79 | 103–106/0.1 | 52 |
| 9 | H | —C₆H₁₃ | — | B(d) | 33 | 80 | 118–126/0.1 | <50 |
| 10 | H | —CH₂—CH₂—OH | — | A(b) | 24 | 80 | 150–160/0.06 | |
| 11 | H | —C₆H₁₁ | — | B(d) | 44 | 65 | 127–132/0.8 | 86 |

TABLE 1-continued

| Ex. No. | R₁ | R₂ | R₃ | Method | Yield | % | B.P. (°C/mm Hg) | M.P. (°C) |
|---|---|---|---|---|---|---|---|---|
| 12 | H |  | — | B(d) | 34 | 29 | 137–140/0.08 | <50 |
| 13 | H |  | — | B(d) | 33 | 67 | 130–146/0.07 | <50 |
| 14 | H |  | — | A(a) | 45 | 24 | 150–180/0.05 | — |
| 1 | H | 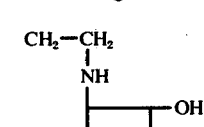 | — | A(a) | 108 | 90 | — | |
| 15 | CH₃ | CH₃ | — | B(c) | 22 | 75 | 86–100/0.1 | 50 |
| 16 | C₂H₅ | C₂H₅ | — | B(d) | 44 | 76 | 85–98/0.06 | — |
| 17 | CH₂—CH₂—OH | CH₂—CH₂—OH | — | A(b) | 24 | 85 | 180–195/0.07 | |
| 2 | piperidinyl | | — | A(b) | 48 | 83 | 110–119/0.07 | |
| 18 | morpholinyl | | — | A(b) | 72 | 76 | 108–122/0.03 | |

| Ex. No. | Analysis Found | | | N % By Protometry | Analysis Theoretical | | |
|---|---|---|---|---|---|---|---|
| | C % | H % | N % | | C % | H % | N % |
| 3 | 43.46 | 7.59 | 8.26 | 8.2 | 44.2 | 7.98 | 8.59 |
| | 43.70 | 7.61 | 8.34 | | | | |
| 5 | 47.09 | 7.88 | 8.07 | 7.84 | 47.4 | 8.46 | 7.91 |
| | 47.00 | 7.85 | 8.12 | | | | |
| 4 | 49.70 | 8.61 | 7.47 | 7.14 | 50.3 | 8.91 | 7.34 |
| | 49.90 | 8.94 | 7.43 | | | | |
| 6 | 52.91 | 9.24 | 6.65 | 6.7 | 52.8 | 9.2 | 6.82 |
| | 52.22 | 8.70 | 6.80 | | | | |
| 7 | 51.88 | 8.82 | 6.29 | 6.67 | 52.8 | 9.2 | 6.82 |
| | 51.44 | 8.91 | 6.42 | | | | |
| 8 | 52.71 | 9.55 | 6.46 | 6.4 | 54.8 | 9.6 | 6.4 |
| | 53.86 | 9.29 | 6.23 | | | | |
| 9 | 58.15 | 10.06 | 5.19 | 5.54 | 58.3 | 10.1 | 5.66 |
| | 57.84 | 10.07 | 5.31 | | | | |
| 10 | 46.30 | 8.29 | 6.4 | 6.75 | 46.37 | 8.27 | 6.76 |
| | 46.50 | 8.43 | 6.56 | | | | |
| 11 | 58.21 | 9.42 | 5.69 | 5.38 | 58.7 | 9.4 | 5.7 |
| | 58.33 | 9.35 | 5.72 | | | | |
| 12 | 59.38 | 6.84 | 5.27 | 5.84 | 60.2 | 7.12 | 5.86 |
| | 59.35 | 6.84 | 5.43 | | | | |
| 13 | 60.88 | 7.17 | 5.03 | 5.55 | 61.6 | 7.52 | 5.53 |
| | 60.76 | 7.55 | 4.97 | | | | |
| 14 | | | | 5.43 | | | 4.53 |
| 1 | 46.98 | 7.94 | 7.8 | 7.88 | 47.75 | 7.95 | 7.95 |
| | 46.58 | 7.82 | 8.0 | | | | |
| 15 | 49.44 | 8.19 | 7.36 | 6.94 | 50.2 | 8.9 | 7.3 |
| | 49.74 | 8.30 | 7.47 | | | | |
| 16 | 54.77 | 9.52 | 5.77 | 6.03 | 54.7 | 9.7 | 6.4 |
| | 54.62 | 9.47 | 6.03 | | | | |
| 17 | 47.27 | 8.26 | 5.84 | 5.6 | 47.8 | 8.42 | 5.57 |
| | 47.29 | 8.39 | 6.03 | | | | |
| 2 | 57.12 | 9.34 | 6.03 | 6.05 | 57.12 | 9.15 | 6.06 |
| 18 | 51.38 | 8.22 | 5.84 | 5.82 | 51.5 | 8.1 | 6.00 |
| | 51.27 | 8.12 | 5.92 | | | | |

TABLE 2

| Ex. No. | R₁ | R₂ | R₃ | X⁻ | Melting Point (°C) | Analysis Found | | | | Analysis Theoretical | | | |
|---|---|---|---|---|---|---|---|---|---|---|---|---|---|
| | | | | | | C % | H % | N % | Cl % | C % | H % | N % | Cl % |
| 20 | CH₃ | CH₃ | CH₃ | CH₃SO₄⁻ | 122 | 37.93 | 7.09 | 4.17 | — | 37.8 | 7.26 | 4.41 | — |
| | | | | | | 38.11 | 7.23 | 4.28 | | | | | |
| 21 | CH₃ | CH₃ |  | Cl⁻ | 178 | 56.56 | 7.30 | 4.17 | 10.95 | 56.6 | 7.55 | 4.41 | 11.2 |
| | | | | | | 56.81 | 7.55 | 4.45 | | | | | |
| 22 | C₂H₅ | C₂H₅ | CH₃ |  | 142 | 53.22 | 7.63 | 3.36 | — | 53.31 | 7.70 | 3.45 | — |
| | | | | | | 53.38 | 7.79 | 3.39 | | | | | |

TABLE 2-continued

| Ex. No. | $R_1$ | $R_2$ | $R_3$ | $X^-$ | Melting Point (°C) | Analysis Found C % | H % | N % | Cl % | Analysis Theoretical C % | H % | N % | Cl % |
|---|---|---|---|---|---|---|---|---|---|---|---|---|---|
| 23 | morpholinyl | | $CH_3$ | $CH_3-\langle\bigcirc\rangle-SO_3^-$ | 124 128 | 51.53 51.56 | 7.00 7.06 | 3.23 | | 51.53 | 6.96 | 3.34 | |
| 24 | piperidinyl | | $CH_3$ | $CH_3SO_3^-$ | 120 122 | 46.01 46.13 | 8.05 7.93 | 4.16 | | 45.59 | 8.24 | 4.09 | |

TABLE 3
Hydrochloride of Bis Dinitrophenylhydrazone of a few Aldehydes

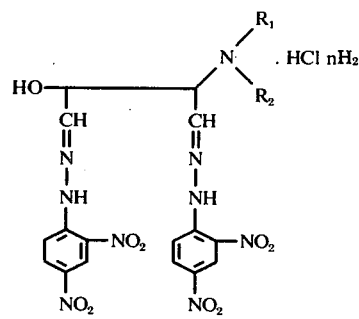

| $R_1$ | $R_2$ | Melting Point with decomposition °C | Analysis Found C % | H % | N % | Analysis-Theoretical C % | H % | N % | for the formula |
|---|---|---|---|---|---|---|---|---|---|
| H | H | 180–188 | 34.78 | 3.02 | 22.46 | 34.95 | 3.66 | 22.92 | $C_{16}H_{15}O_9N_9 \cdot HCl \cdot 2H_2O$ |
| H | —$CH_3$ | 160–165 | 37.44 | 3.51 | 22.19 | 37.40 | 3.69 | 23.09 | $C_{17}H_{17}O_9N_9 \cdot HCl \cdot H_2O$ |
| H | —$C_2H_5$ | 160–168 | 39.31 | 3.58 | 22.48 | 38.61 | 3.96 | 22.51 | $C_{18}H_{19}O_9N_9 \cdot HCl \cdot H_2O$ |
| H | —$C_3H_7$ | 156–162 | 39.75 | 4.18 | 21.87 | 39.76 | 4.21 | 21.96 | $C_{19}H_{21}O_9N_9 \cdot HCl \cdot H_2O$ |
| H | —CH(CH_3)_2 | 160–175 | 40.29 | 4.11 | 21.63 | 39.76 | 4.21 | 21.96 | $C_{19}H_{21}O_9N_9 \cdot HCl \cdot H_2O$ |
| H | —$C_4H_9$ | 150–162 | 39.77 | 4.24 | 21.94 | 40.85 | 4.45 | 21.44 | $C_{20}H_{23}O_9N_9 \cdot HCl \cdot H_2O$ |
| H | —$C_6H_{13}$ | 137–142 | 42.84 | 4.61 | 20.47 | 42.89 | 4.90 | 20.46 | $C_{22}H_{27}O_9N_9 \cdot HCl \cdot H_2O$ |
| H | —Ph | 164–172 | 42.81 | 4.30 | 20.48 | 43.03 | 4.59 | 20.53 | $C_{22}H_{25}O_9N_9 \cdot HCl \cdot H_2O$ |
| H | —$CH_2$—Ph | 155–165 | 44.10 | 3.56 | 20.42 | 44.41 | 3.88 | 20.27 | $C_{23}H_{21}O_9N_9 \cdot HCl \cdot H_2O$ |

EXAMPLES OF USE

Example 34

The following tanning composition is prepared

| | |
|---|---|
| 8% solution of 2-amino 3-hydroxy succinic aldehyde | 40 ml |
| ethyl alcohol, 96° titer | 40 ml |
| white glycerol | 2 ml |
| perfume | 1 g |
| $Na_2CO_3$, q.s.p. for pH = 2 | |
| water, q.s.p. | 100 ml |

This composition is applied regularly to all parts of the body that one wishes to tan.

At the end of 2 or 3 minutes a light coloration appears which after 15 minutes assumes a very natural brown tone. This shade is rather resistant. However, if the shade is considered to be too dark, it can be lightened by washing with water and soap, makeup remover milk or eau de Cologne.

A product of this kind is much appreciated especially for "harmonizing" or "touching up" e.g. when there are white marks left by eyeglass frames on the nose or by shoulder straps on the shoulders.

Example 35

The following composition in the form of white milk is prepared:

| | |
|---|---|
| cetyl stearyl alcohol, partly oxyethylenated (sold commercially as "Sipol wax" by the Sinnova company (France) | 2.5 g |

-continued

| | |
|---|---|
| wheat starch | 2 g |
| a mixture of methyl, ethyl, butyl and benzyl esters of para hydroxybenzoic acid (sold commercially as "Nipa ester 82521" by Nipa company (US) | 0.19 g |
| phenyl polysiloxane (sold commercially as "Rhodorsil oil 47 V.300" by Rhone-Poulenc company (France) | 0.2 g |
| 10% solution of 2-methylamino 3-hydroxysuccinic aldehyde | 20 g |
| Na$_2$CO$_3$, 2N, q.s.p. for pH 3 | |
| perfume | 0.5 g |
| water, q.s.p. | 100 g |

When evenly applied to the skin, this milk affords a golden coloration in less than 10 minutes. The color reaches its maximum in at least an hour, looking just like natural tan. The coloration is resistant to baths, even in sea water.

EXAMPLE 36

The following oleo-alcohol composition is prepared:

| | |
|---|---|
| colza oil | 2 g |
| isopropyl myristate | 25 g |
| ethyl alcohol, 96° titer | 60 g |
| perfume | 0.5 g |
| 18% solution of 2-benzylamino 3-hydroxysuccinic aldehyde (the pH being adjusted to 3 by means of Na$_2$CO$_3$ | 12.5 g |

This composition is introduced into aerosol cans and, after sealing, 70 g of dichlorodifluoromethane are added. This composition is sprayed on any part of the body that is to be tanned. At the end of 15 minutes a light coloration begins to appear, which then darkens to a bronzed hue. This color resists fresh water, sea water, washing with soap, and makeup removers.

EXAMPLES 37

There is prepared a solution of 2-amino 3-hydroxy succinic aldehyde, by heating for 10 minutes in a boiling water bath, 519 mg of 2,5-dimethoxy 3-amino 4-hydroxy tetrahydrofuran in 10 cc N HCl. The pH of this solution is adjusted to between 3 and 4 by the addition thereto of sodium carbonate.

Bleached hair is impregnated with the above solution and heated under a hood for 30 to 45 minutes. At the end of this contact period, the hair is shampooed, rinsed and dried. The thus treated hair has an improved appearance, is flexible and more lively.

EXAMPLE 38

A solution of 3-hydroxy 2-propylaminosuccinic aldehyde is prepared by heating for one hour in a boiling water bath 2.78 g of 2,5-dimethoxy 4-hydroxy 3-propylamino tetrahydrofuran in 33.5 cc 1N HCl. The pH of this solution is adjusted to between 3 and 4 by the addition thereto of sodium carbonate.

As indicated in Example 37 previously bleached hair is treated with the solution thus prepared. The results are just as good as those reported in Example 37.

EXAMPLE 39

A solution of 2,2'-ethylene diamino bis (3-hydroxysuccinic) aldehyde is prepared by heating for 1 hour over a boiling water bath, 608 mg of 3,3' ethylene diamino bis(4-hydroxy 2,5-dimethoxy) tetrahydrofuran in 10 ml 1N HCl. The pH of this solution is adjusted to 3.5 by the addition thereto of sodium carbonate.

As indicated in Example 37, previously bleached hair is treated with the solution thus prepared. The results are just as good as those achieved in Examples 37 and 38.

EXAMPLE 40

A solution of 3-hydroxy 2-piperidino succinic aldehyde is prepared by heating for 5 hours over a boiling water bath 3.5 g of 2,5-dimethoxy 3-hydroxy 4-piperidino tetrahydrofuran in 40 cc of 1N HCl. The pH of this solution is adjusted to 4 by the addition thereto of sodium carbonate.

As indicated in Example 37, previously bleached hair is treated with the solution thus prepared and the results obtained are just as good as those reported in Examples 37–39.

EXAMPLE 41

A solution of quaternary ammonium salt of 3-hydroxy 2-trimethylammonium succinic aldehyde is prepared by dissolving 2.53 g of 2,5-dimethoxy 4-hydroxy 3-trimethylammonium tetrahydrofuran methosulfate in 15 ml 1N NaOH and adding to this solution after it has stood overnight, at ambient temperature, 15 ml of 2N HCl and heating for 43 hours over a boiling water bath. The pH of this solution is adjusted between 3 and 4 by the addition thereto of sodium carbonate.

As indicated in Example 37, previously bleached hair is treated with the solution thus prepared. The results obtained are just as good as in the previous examples.

EXAMPLE 42

The following composition is prepared:

| | |
|---|---|
| succinic aldehyde | 50 cc |
| ethyl alcohol, 96° titer | 40 cc |
| glycerine | 2 cc |
| perfume | 0.1 cc |
| sodium bicarbonate, q.s.p. | pH 3 |
| water, q.s.p. | 100 cc |

The resulting clear brown liquid when applied to those parts of the body desired to be tanned, imparts thereto in about one-half hour, an amber shade that can be essentially removed by washing with soap water.

EXAMPLE 43

The following composition is prepared: 0.372 M solution of 2-butylamino 3-hydroxy

| | |
|---|---|
| succinic aldehyde | 15 cc |
| oleyl alcohol condensed with 10 moles ethylene oxide | 5 g |
| carboxymethyl cellulose | 2 g |
| orthohydroxy quinoline sulfate | 0.1 g |
| silicone oil | 1 g |
| 2N sodium carbonate, q.s.p. | pH 3 |
| perfume | 1 g |
| water, q.s.p. | 100 g |

This composition is applied to the skin to be tanned. The desired, very natural brown color appears ten minutes following application. The resistance of the coloration achieved to even soapy water increases with the length of the application time.

Tanning Milk

| | |
|---|---|
| cetyl stearyl alcohol condensed with 13 moles ethylene oxide | 7 g |
| phenyl polysiloxane (sold under the name "Rhodorsil Oil 47 V300" by Rhone-Poulenc company) | 1 g |
| diethyleneglycol stearate | 6 g |
| methyl parahydroxy benzoate | 0.1 g |
| propyl parahydroxy benzoate | 0.1 g |
| 0.411 M solution of 2-hexylamino 3-hydroxy succinic aldehyde | 25 cc |
| 2N sodium carbonate, q.s.p. | pH 2.5 |
| water, q.s.p. | 100 g |

When applied to the skin, this bronzing or tanning milk reaches maximum intensity of coloration in about two hours. The coloration is a very natural golden shade which resists removal by water.

EXAMPLE 45

Tanning Cream

| | |
|---|---|
| cetyl stearyl alcohol condensed with 13 moles of ethylene oxide | 2.6 g |
| cetyl alcohol | 2.6 g |
| stearic acid | 0.6 g |
| castor oil | 6.85 g |
| sweet almond oil | 1.3 g |
| $C_{12}$–$C_{14}$ alcohol condensed with 10.5 moles ethylene oxide | 0.3 g |
| ethyl para amino benzoate | 0.2 g |
| isopropyl myristate | 4.5 g |
| perfume | 0.3 g |
| 0.372 M solution of 2-cyclohexyl amino 3-hydroxy succinic aldehyde | 35 cc |
| 2N sodium carbonate, q.s.p. | pH 3.5 |
| water, q.s.p. | 100 cc |

The resulting cream is colored light beige and when applied on the portions of the skin to be tanned, the coloration starts to appear in about 15 minutes and reaches its maximum intensity in about 2 hours. The color obtained is a petty natural chestnut shade which resists quite well even soapy water.

EXAMPLE 46

10 grams of previously bleached hair are impregnated with 25 cc of a solution of 0.425 M 2-hydroxy 3-trimethylammonio succinic aldehyde prepared by acid hydrolysis of the corresponding tetrahydrofuran. The pH of the solution is adjusted to 3 by the addition thereto of sodium bicarbonate. The solution is permitted to remain in contact with the hair for 30 minutes at a temperature of 50° C, after which the hair is rinsed and dried. As a result of this treatment the hair has an improved appearance, is more flexible and more soft.

EXAMPLE 47

To hair which has previously been permanently waved there is applied a 0.512 M solution of 2-hydroxy 3-dimethyl benzyl ammonio succinic aldehyde prepared by acid hydrolysis of the corresponding tetrahydrofuran. The pH of said solution being adjusted to 4 by the addition thereto of sodium bicarbonate. This solution is permitted to remain in contact with the hair for 40 minutes at 30° C, after which the hair is rinsed and dried. The thus treated hair has a very agreeable look and is more soft to the touch than the hair prior to said treatment.

EXAMPLE 48

Bleached hair is impregnated for a period of 30 minutes at 30° C with a 0.362 M solution of 2-hydroxy 3-diethylmethyl ammonio succinic aldehyde prepared by acid hydrolysis of the corresponding tetrahydrofuran. The pH of the solution is adjusted to 3.5 by the addition thereto of sodium bicarbonate. The thus treated hair is then rinsed after which a hair setting lotion comprising 40% aqueous solution of a copolymer of vinyl pyrrolidone and vinyl acetate having a viscosity of 3.5 to 4 centiposes in 5% solution in ethanol having a pH of 3.5 is applied thereto. The hair is then rolled on curlers and dried. Excellent results are obtained including the imparting of a brilliant sheen to the hair.

EXAMPLE 49

Previously bleached hair is impregnated with a 0.437 M solution of 2-hydroxy 3-(methyl morpholino) succinic anhydride, the pH of which had been adjusted to 2.5 by the addition thereto of powdered sodium carbonate. The solution remained in contact with the hair for a period of 30 minutes at a temperature of 45° C. The hair was then rinsed and set in the customary way.

After drying the hair is more easy to style and less electric than hair not treated with said solution.

EXAMPLE 50

To previously bleached hair there is applied for a period of about 30 minutes at 50° C the following solution:

| | |
|---|---|
| 0.484 M solution of 2-hydroxy 3-(methyl piperidino) succinic aldehyde | 100 cc |
| sodium bicarbonate, q.s.p. | pH 3 |

Thereafter the hair is rinsed, rolled on curlers and dried under a hood. The hair thus treated is lively and less electric and more easy to style than hair not treated as described.

EXAMPLE 51

To hair that has been previously bleached and then dyed, there is applied a 0.353 M solution of 2-diethylamino 3-hydroxy succinic aldehyde, the pH of which has been adjusted to 2.5 by the addition thereto of sodium carbonate. The solution is permitted to remain in contact with the hair for a period of 30 minutes at 50° C. The hair is then rinsed, set in the usual fashion and dried under a hood. The thus treated hair is more brilliant and less subject to tangling than hair not treated with the solution described above.

EXAMPLE 52

Previously bleached hair is shampooed with an acidic cationic shampoo composition and then dried. Thereafter the hair is impregnated with 100 cc of a 0.268 M solution of 2-bis (β-hydroxyethyl amono 3-hydroxy succinic aldehyde, the pH of which has been adjusted to 2.5 by the addition thereto of sodium bicarbonate, for a period of about 30 minutes at 45° C. To the thus treated hair there is then applied the following hair setting solution:

| | |
|---|---|
| solution in ethanol | 5 g |
| ethyl alcohol, 96° titer | 25 cc |
| trimethyl cetyl ammonium bromide | 0.1 g |
| powdered sodium bicarbonate, q.s.p. | pH 2.5 |

| water, q.s.p. | 100 cc |
|---|---|

The hair is then rolled on curlers and again saturated with the above hair setting solution. After drying, the hair is lively and holds a good set.

What is claimed is:

1. A process for strengthening the hair for the purpose of improving its cosmetic qualities comprising applying to the hair for a period of 5 to 60 minutes at a temperature of 15°–50° C a composition comprising a solution in a solvent selected from the group consisting of water and an aqueous alcohol solution wherein the alcohol component is selected from the group consisting of ethanol and isopropanol, of 2–25 percent by weight of said composition of a dialdehyde selected from the group consisting of
   1. an aminated γ-dialdehyde having the formula

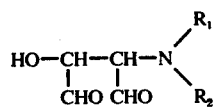

wherein $R_1$ and $R_2$ each independently are selected from the group consisting of hydrogen, alkyl having 1–6 carbon atoms, hydroxy alkyl wherein the alkyl moiety has 1–6 carbon atoms, cycloalkyl having 3–6 carbon atoms, phenyl, benzyl, (2,5-dialkoxy-4-hydroxy)-3-tetrahydrofuryl wherein each of the alkoxy moieties has 1–4 carbon atoms, β-N-aminoethyl wherein each of the alkoxy moieties has 1–4 carbon atoms, and together with the nitrogen atom to which they are attached form a heterocycle selected from the group consisting of piperidinyl and morpholinyl; and
   2. a quaternary ammonium salt having the formula

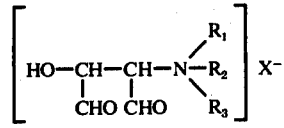

wherein $R_1$ and $R_2$ each independently are selected from the group consisting of alkyl having 1–6 carbon atoms, hydroxyalkyl wherein the alkyl moiety has 1–6 carbon atoms, cycloalkyl having 3–6 carbon atoms, phenyl, benzyl, (2,5-dialkoxy-4-hydroxy)-3-tetrahydrofuryl wherein each of the alkoxy moieties has 1–4 carbon atoms, β-N-aminoethyl wherein each of the alkoxy moieties has 1–4 carbon atoms and together with the nitrogen atom to which they are attached form a heterocycle selected from the group consisting of piperidinyl and morpholinyl, $R_3$ is selected from the group consisting of lower alkyl having 1–4 carbon atoms and benzyl, and $X^-$ represents a member selected from the group consisting of chloride, bromide, iodide, methosulfate, ethosulfate, paratoluene sulfonate and methane sulfonate, said composition having a pH between 1.5 and 9.

2. The process of claim 1 wherein said dialdehyde is selected from the group consisting of 2-amino-3-hydroxy succinic aldehyde, 3-hydroxy-2-propylamino succinic aldehyde, 2,2'-ethylene diamino bis (3-hydroxy succinic) aldehyde 3-hydroxy-2-piperidino succinic aldehyde, quaternary ammonium salt of 3-hydroxy-2-trimethyl ammonium succinic aldehyde, 2-hydroxy-3-dimethyl benzyl ammonio succinic aldehyde, 2-hydroxy-3-diethylmethylammonio succinic aldehyde, 2-hydroxy-3-(methyl morpholino) succinic aldehyde, 2-hydroxy-3-(methyl piperidino) succinic aldehyde, 2-diethylamino-3-hydroxy succinic aldehyde and 2-bis(β-hydroxyethylamino)-3-hydroxy succinic aldehyde.

3. The process of claim 1 wherein said dialdehyde is 2-hexylamino-3-hydroxy succinic aldehyde.

4. The process of claim 1 wherein said composition has a pH between 2–5.

5. The process of clam 1 wherein said hair has been previously bleached or subjected to a permanent wave operation.

6. The process of claim 1 wherein said composition is applied to said hair after a first stage reduction of a permanent wave operation and before a second stage neutralization of said permanent wave operation.

7. A cosmetic hair strengthening composition comprising a solution in a solvent selected from the group consisting of water and an aqueous alcohol solution wherein the alcohol component is selected from the group consisting of ethanol and isopropanol, of about 2 to about 25 percent by weight of said composition of a dialdehyde selected from the group consisting of
   1. an aminated γ-dialdehyde having the formula

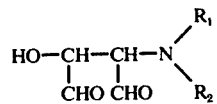

wherein $R_1$ and $R_2$ each independently are selected from the group consisting of hydrogen, alkyl having 1–6 carbon atoms, hydroxy alkyl wherein the alkyl moiety has 1–6 carbon atoms, cycloalkyl having 3–6 carbon atoms, phenyl, benzyl, (2,5-dialkoxy-4-hydroxy)-3-tetrahydrofuryl wherein each of the alkoxy moieties has 1–4 carbon atoms, β-N-amino ethyl wherein each of the alkoxy moieties has 1–4 carbon atoms, and together with the nitrogen atom to which they are attached form a heterocycle selected from the group consisting of piperidinyl and morpholinyl; and
   2. a quaternary ammonium salt having the formula

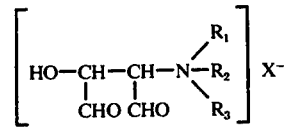

wherein $R_1$ and $R_2$ each independently are selected from the group consisting of alkyl having 1–6 carbon atoms, hydroxyalkyl wherein the alkyl moiety has 1;14 6 carbon atoms, cycloalkyl having 3–6 carbon atoms, phenyl, benzyl, (2,5-dialkoxy-4-hydroxy)-3-tetrahydrofuryl wherein each of the alkoxy moieties has 1–4 carbon atoms, β-N-aminoethyl wherein each of the alkoxy moieties has 1–4 carbon atoms and together with the nitrogen atom to which they are attached form a heterocycle selected from the group consisting of piperidinyl and morpholinyl, $R_3$ is selected from the group consisting of lower alkyl having 1–4 carbon atoms and benzyl, and $X^-$ represents a member selected from the group consisting of chloride, bromide, iodide, methosulfate, ethosulfate, paratoluene sulfonate and methane sufonate, said composition having a pH between 1.5 and 9.

8. The cosmetic hair strengthening composition of claim 7 wherein said dialdehyde is selected from the group consisting of 2-amino-3-hydroxy succinic aldehyde, 3-hydroxy-2-propylamino succinic aldehyde, 2,2'-ethylene diamino bis (3-hydroxy succinic) aldehyde, 3-hydroxy-2-piperidino succinic aldehyde, quaternary ammonium salt of 3-hydroxy-2-trimethyl ammonium succinic aldehyde, 2-hydroxy-3-dimethyl benzyl ammonio succinic aldehyde, 2-hydroxy-3-diethylmethylammonio succinic aldehyde, 2-hydroxy-3-(methyl morpholino) succinic aldehyde, 2-hydroxy-3-(methyl piperidino) succinic aldehyde, 2-diethylamino-3-hydroxy succinic aldehyde and 2-bis($\beta$-hydroxyethylamino)-3-hydroxy succinic aldehyde.

9. The cosmetic hair strengthening composition of claim 7 wherein said dialdehyde is 2-hexylamino-3-hydroxy succinic aldehyde.

10. The composition of claim 7 wherein said composition has a pH between 2–5.

11. The composition of claim 7 wherein said dialdehyde is present in an amount of about 3–18 percent by weight of said composition.

* * * * *